(12) United States Patent
Banks et al.

(10) Patent No.: US 9,739,754 B2
(45) Date of Patent: Aug. 22, 2017

(54) TRANSDUCER POSITION GUIDE (71) Applicant: UNITED TECHNOLOGIES CORPORATION, Farmington, CT (US)

(72) Inventors: Anton G. Banks, Manchester, CT (US); Steven Taffet, South Windsor, CT (US); Christopher Laxton, Vernon, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 330 days.

(21) Appl. No.: 14/449,813

(22) Filed: Aug. 1, 2014

(65) Prior Publication Data
US 2015/0122031 A1    May 7, 2015

Related U.S. Application Data

(60) Provisional application No. 61/898,822, filed on Nov. 1, 2013.

(51) Int. Cl.
*G01N 29/265* (2006.01)

(52) U.S. Cl.
CPC ...... *G01N 29/265* (2013.01); *G01N 2291/044* (2013.01); *G01N 2291/101* (2013.01); *G01N 2291/2638* (2013.01); *G01N 2291/2693* (2013.01)

(58) Field of Classification Search
CPC ............. G01N 29/223; G01N 29/4445; G01N 29/265; G01N 2291/044
USPC ......................................................... 73/634
See application file for complete search history.

(56) References Cited

U.S. PATENT DOCUMENTS

| | | | |
|---|---|---|---|
| 4,146,967 A * | 4/1979 | Rohner | G01B 5/0002 33/530 |
| 6,985,430 B1 * | 1/2006 | Villiard | G11B 5/584 360/261.1 |
| 7,706,101 B2 * | 4/2010 | Vanderheyden | G11B 5/584 360/78.12 |
| 9,334,066 B2 * | 5/2016 | Tapia | B64F 5/0045 |
| 9,347,759 B2 * | 5/2016 | Kane | G01B 5/00 |

* cited by examiner

*Primary Examiner* — J M Saint Surin
(74) *Attorney, Agent, or Firm* — Cantor Colburn LLP (57) ABSTRACT

The present disclosure relates generally to a transducer position guide. The transducer position guide may be attached to a component to be measured, such as an airfoil, and controls a path traversed by the transducer during a measurement process.

20 Claims, 6 Drawing Sheets

TRANSDUCER POSITION GUIDE

CROSS-REFERENCE TO RELATED APPLICATION

The present application claims the benefit of and incorporates by reference herein the disclosure of U.S. Ser. No. 61/898,822 filed Nov. 1, 2013.

GOVERNMENT LICENSE RIGHTS

This invention was made with government support under Contract No. N00019-02-C-3003 awarded by the United States Air Force. The government has certain rights in the invention.

TECHNICAL FIELD OF THE DISCLOSURE

The present disclosure is generally related to transducers and, more specifically, to transducer position guide.

BACKGROUND OF THE DISCLOSURE

Inspection of components using transducers positioned at the component surface is performed for a wide variety of component types. As an example, airfoils used in gas turbine engines may be cast as single crystal airfoils. An ultrasonic transducer may be used to inspect the airfoil to inspect grain boundaries to detect defects in the casting. For example, an ultrasonic transducer may be able to detect a sliver grain, void or other defect that occurred during the single crystal casting or heat treating process. In order to obtain usable data from the ultrasonic transducer, the position and orientation of the transducer must be tightly controlled as it is moved across the surface to be measured. This is true for many types of transducers when used to inspect many types of components and is not limited to gas turbine airfoils. For the airfoil application, the use of the transducer may be further complicated when the transducer measurements are made on an airfoil that is inside an assembled gas turbine engine, such as during an "on wing" inspection of the engine. In many such instances, the airfoil being inspected cannot be directly viewed by the personnel performing the inspection, and may only be reached by the use of specialized tools. Therefore, improvements for positioning transducers are still needed in the art.

SUMMARY OF THE DISCLOSURE

In one embodiment, a transducer position guide configured for application to an airfoil including an airfoil root, an airfoil body, an airfoil leading edge and an airfoil trailing edge is disclosed, the transducer position guide comprising: a transducer head guide rail; at least one arm extending from the transducer head guide rail; and a transducer head adaptor configured to receive a transducer head, the transducer head adaptor disposed in sliding contact with the transducer head guide rail.

In another embodiment, a transducer position guide configured for application to an airfoil including an airfoil root, an airfoil body, an airfoil leading edge and an airfoil trailing edge is disclosed, the transducer position guide comprising: a first support; at least one arm extending from the first support; a transducer head guide rail coupled to the at least one arm; and a transducer head adaptor configured to receive a transducer head, the transducer head adaptor disposed in sliding contact with the transducer head guide rail.

Other embodiments are also disclosed.

BRIEF DESCRIPTION OF THE DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein.

DETAILED DESCRIPTION OF THE DISCLOSED EMBODIMENTS

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Figure 1:
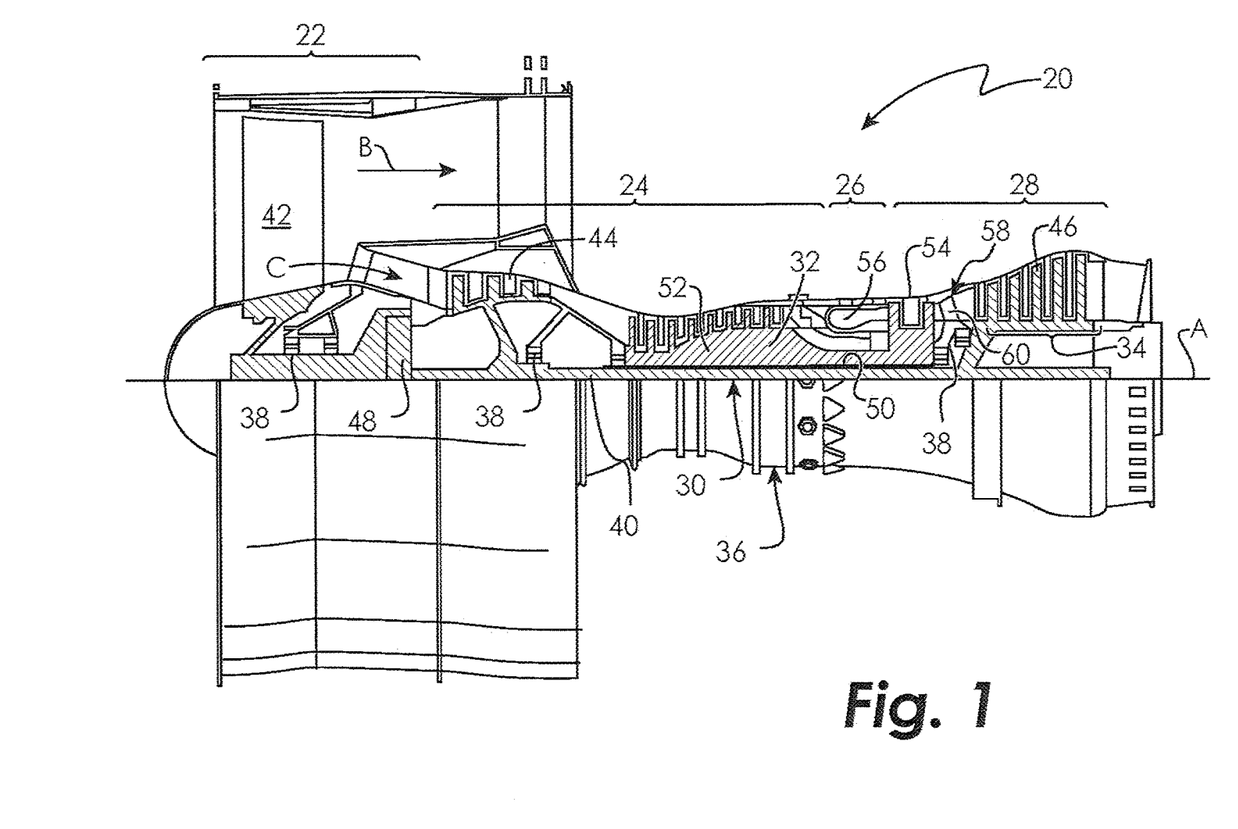
FIG. 1 is a schematic partial cross-sectional view of a gas turbine engine in an embodiment.

FIG. 1 schematically illustrates a gas turbine engine 20. The gas turbine engine 20 is disclosed herein as a two-spool turbofan that generally incorporates a fan section 22, a compressor section 24, a combustor section 26 and a turbine section 28. Alternative engines might include an augmentor section (not shown) among other systems or features. The fan section 22 drives air along a bypass flow path B in a bypass duct defined within a nacelle 15, while the compressor section 24 drives air along a core flow path C for compression and communication into the combustor section 26 then expansion through the turbine section 28. Although depicted as a two-spool turbofan gas turbine engine in the disclosed non-limiting embodiment, it should be understood that the concepts described herein are not limited to use with two-spool turbofans as the teachings may be applied to other types of turbine engines including three-spool architectures.

The exemplary engine 20 generally includes a low speed spool 30 and a high speed spool 32 mounted for rotation about an engine central longitudinal axis A relative to an engine static structure 36 via several bearing systems 38. It should be understood that various bearing systems 38 at various locations may alternatively or additionally be provided, and the location of bearing systems 38 may be varied as appropriate to the application.

The low speed spool 30 generally includes an inner shaft 40 that interconnects a fan 42, a low pressure compressor 44 and a low pressure turbine 46. The inner shaft 40 is connected to the fan 42 through a speed change mechanism, which in exemplary gas turbine engine 20 is illustrated as a geared architecture 48 to drive the fan 42 at a lower speed than the low speed spool 30. The high speed spool 32 includes an outer shaft 50 that interconnects a high pressure compressor 52 and high pressure turbine 54. A combustor 56 is arranged in exemplary gas turbine 20 between the high pressure compressor 52 and the high pressure turbine 54. A mid-turbine frame 57 of the engine static structure 36 is arranged generally between the high pressure turbine 54 and the low pressure turbine 46. The mid-turbine frame 57 further supports bearing systems 38 in the turbine section 28. The inner shaft 40 and the outer shaft 50 are concentric and rotate via bearing systems 38 about the engine central longitudinal axis A which is collinear with their longitudinal axes.

The core airflow is compressed by the low pressure compressor 44 then the high pressure compressor 52, mixed and burned with fuel in the combustor 56, then expanded over the high pressure turbine 54 and low pressure turbine 46. The mid-turbine frame 57 includes airfoils 59 which are in the core airflow path C. The turbines 46, 54 rotationally drive the respective low speed spool 30 and high speed spool 32 in response to the expansion. It will be appreciated that each of the positions of the fan section 22, compressor section 24, combustor section 26, turbine section 28, and fan drive gear system 48 may be varied. For example, gear system 48 may be located aft of combustor section 26 or even aft of turbine section 28, and fan section 22 may be positioned forward or aft of the location of gear system 48.

The engine 20 in one example is a high-bypass geared aircraft engine. In a further example, the engine 20 bypass ratio is greater than about six (6), with an example embodiment being greater than about ten (10), the geared architecture 48 is an epicyclic gear train, such as a planetary gear system or other gear system, with a gear reduction ratio of greater than about 2.3 and the low pressure turbine 46 has a pressure ratio that is greater than about five. In one disclosed embodiment, the engine 20 bypass ratio is greater than about ten (10:1), the fan diameter is significantly larger than that of the low pressure compressor 44, and the low pressure turbine 46 has a pressure ratio that is greater than about five 5:1. Low pressure turbine 46 pressure ratio is pressure measured prior to inlet of low pressure turbine 46 as related to the pressure at the outlet of the low pressure turbine 46 prior to an exhaust nozzle. The geared architecture 48 may be an epicycle gear train, such as a planetary gear system or other gear system, with a gear reduction ratio of greater than about 2.3:1. It should be understood, however, that the above parameters are only exemplary of one embodiment of a geared architecture engine and that the present invention is applicable to other gas turbine engines including direct drive turbofans.

A significant amount of thrust is provided by the bypass flow B due to the high bypass ratio. The fan section 22 of the engine 20 is designed for a particular flight condition—typically cruise at about 0.8 Mach and about 35,000 feet. The flight condition of 0.8 Mach and 35,000 ft., with the engine at its best fuel consumption—also known as "bucket cruise Thrust Specific Fuel Consumption ('TSFC')"—is the industry standard parameter of lbm of fuel being burned divided by lbf of thrust the engine produces at that minimum point. "Low fan pressure ratio" is the pressure ratio across the fan blade alone, without a Fan Exit Guide Vane ("FEGV") system. The low fan pressure ratio as disclosed herein according to one non-limiting embodiment is less than about 1.45. "Low corrected fan tip speed" is the actual fan tip speed in ft/sec divided by an industry standard temperature correction of $[(Tram\,°\,R)/(518.7°\,R)]0.5$. The "Low corrected fan tip speed" as disclosed herein according to one non-limiting embodiment is less than about 1150 ft/second.

FIGS. 2-6 schematically illustrate a transducer position guide in an embodiment, indicated generally at 100. The transducer position guide 100 may be positioned adjacent the surface of an airfoil 102. The transducer position guide 100 includes a transducer head guide rail 104, a first arm 106 and a second arm 108. First arm 106 and second arm 108 extend substantially perpendicularly from the transducer head guide rail 104 in an embodiment. Multiple head guide rails 104 may be provided within one transducer position guide 100 in an embodiment. The first arm 106 and the second arm 108 may be curved such that they substantially match the contour of the airfoil 102. The transducer position guide 100 may include at least one standoff 110 disposed on second arm 108, wherein the at least one standoff 110 rests upon a root 112 of the airfoil 102 in an embodiment. The standoff 110 maintains a desired radial location of the transducer position guide 100. In one embodiment, only a single standoff 110 is provided.

Figure 2:
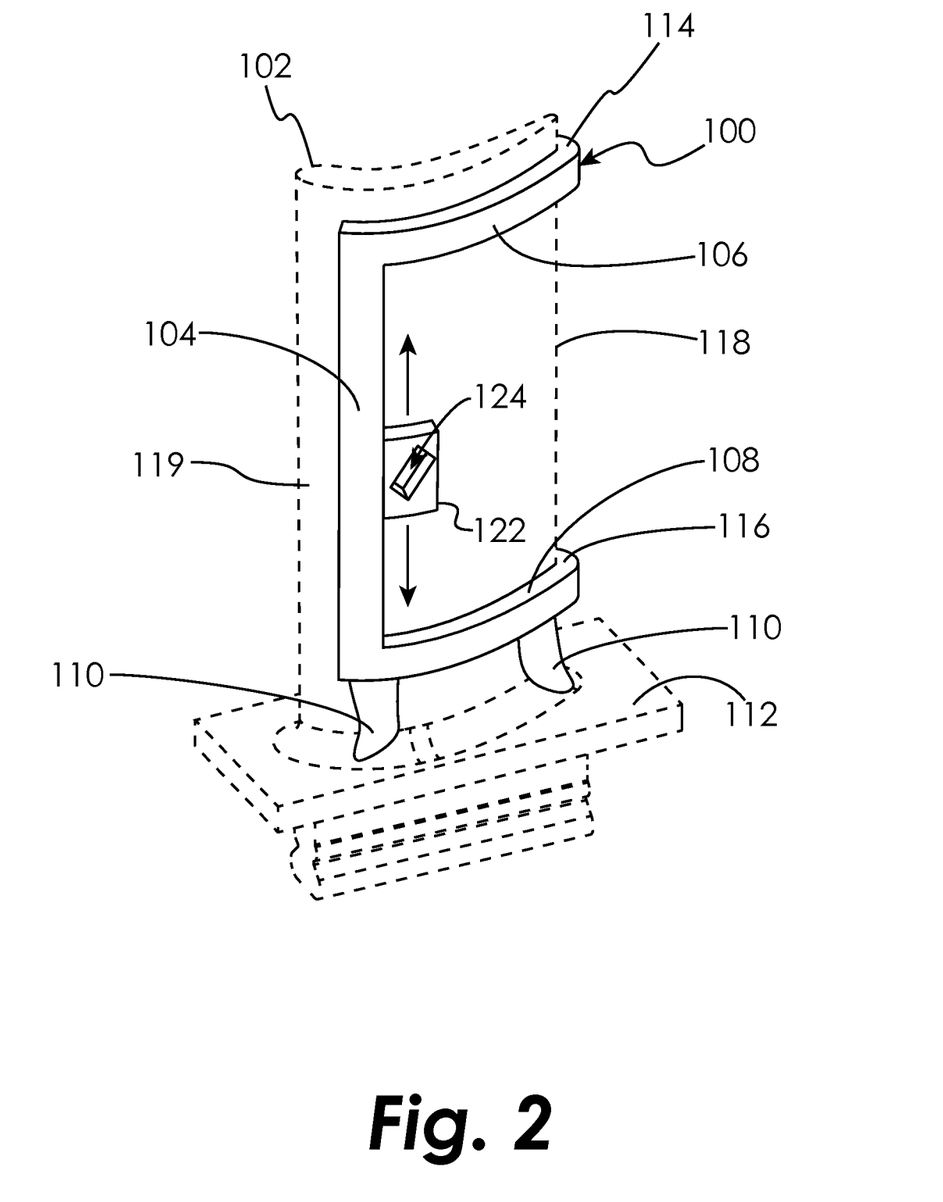
FIG. 2 is a schematic perspective view of a transducer position guide in an embodiment.
Figure 3:
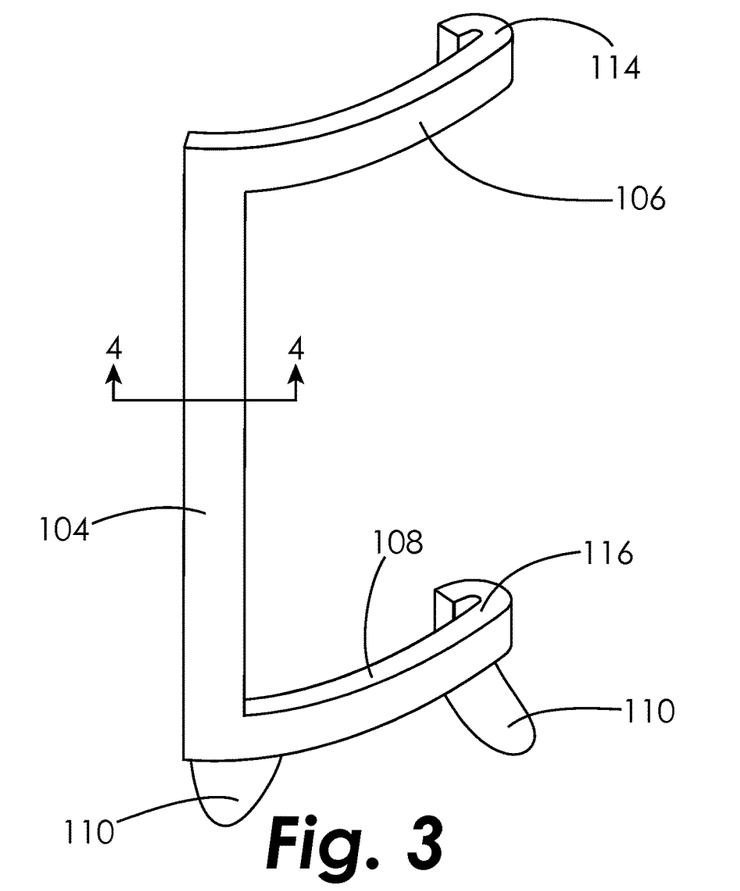
FIG. 3 is a schematic perspective view of a transducer position guide in an embodiment.
Figure 4:
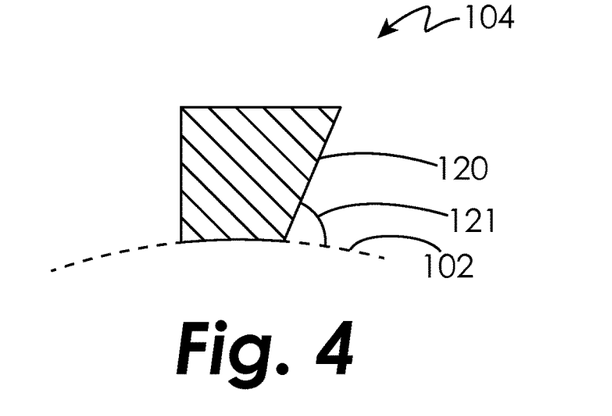
FIG. 4 is a schematic cross-sectional view of a transducer position guide in an embodiment.

The first arm 106 includes a first hooked distal portion 114 and the second arm 108 includes a second hooked distal portion 116 in an embodiment. Hooked distal portions 114 and 116 may be engaged with the airfoil 102 such that they wrap around the trailing edge 118 of the airfoil 102 in order to maintain the correct axial location of the transducer position guide 100. In an embodiment, the transducer position guide 100 may have one or more hooked proximal portions (not shown) that wrap around the leading edge 119 of the airfoil 102. The provision of hooked proximal portions may be provided with or without the provision of hooked distal portions 114. The position of the transducer head guide rail 104 may be located at any desired location on the airfoil 102. In an embodiment, the aft surface 120 of the transducer head guide rail 104 is located parallel to a stacking axis of the airfoil 102. As shown in FIG. 4, the aft surface 120 of the transducer head guide rail 104 may form an acute angle 121 with the surface of the airfoil 102 in an embodiment.

Figure 5:
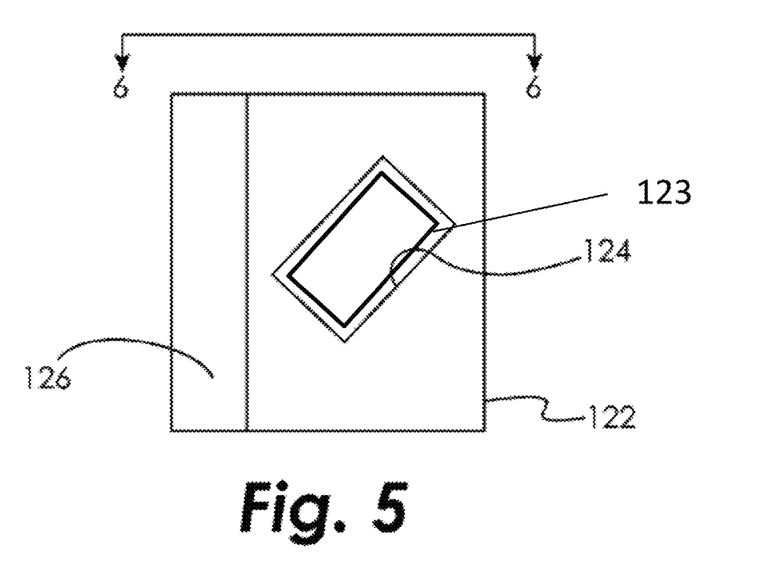
FIG. 5 is a schematic plan view of a transducer head adaptor in an embodiment.
Figure 6:
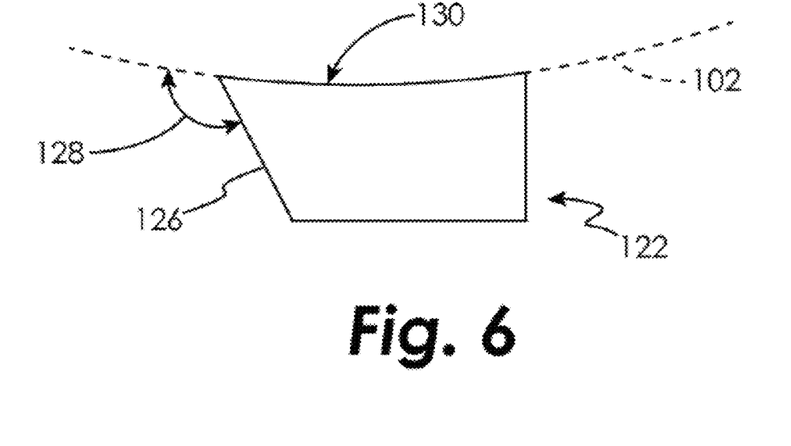
FIG. 6 is a schematic elevational view of a transducer head adaptor in an embodiment.

A transducer or transducer head 123 may be positioned within a transducer head adaptor 122. The transducer head adaptor 122 includes a transducer receiving cavity 124 formed therein in an embodiment. The transducer receiving cavity 124 may be sized and shaped to receive the transducer or transducer head 123 to be used and to maintain a desired orientation between the transducer or transducer head 123 and the surface of the airfoil 102. The transducer head adaptor 122 may be disposed in sliding contact with the transducer head guide rail 104. As shown in FIGS. 5-6, the transducer head adaptor 122 includes a forward surface 126 that contacts the aft surface 120 of the transducer head guide rail 104 when in use. As shown in FIG. 6, the forward surface 126 of the transducer head adaptor 122 may form an obtuse angle 128 with the surface of the airfoil 102, wherein the angle 121 plus the angle 128 is substantially 180 degrees in an embodiment. The surface 130 of the transducer head adaptor 122 that contacts the airfoil 102 may be formed with a radius of curvature approximately equal to an average radius of curvature of the airfoil 102 along the measurement path in an embodiment.

In use, the hooked distal portions 114 and 116 of the transducer position guide 100 are engaged with the trailing edge 118 of the airfoil 102, while the standoff(s) 110 rest upon the root 112. A transducer (not shown) is mounted in the transducer receiving cavity 124 of the transducer head adaptor 122. The transducer may be coupled to any desired test equipment by, for example, a wired or wireless connection. The transducer head adaptor 122 forward surface 126 is engaged with the transducer head guide rail 104 aft surface 120 to position the transducer at a desired measurement location. The transducer head adaptor 122 may then be translated along the transducer head guide rail 104 between the first arm 106 and the second arm 108 in order to produce a series of measurements.

Figure 7:
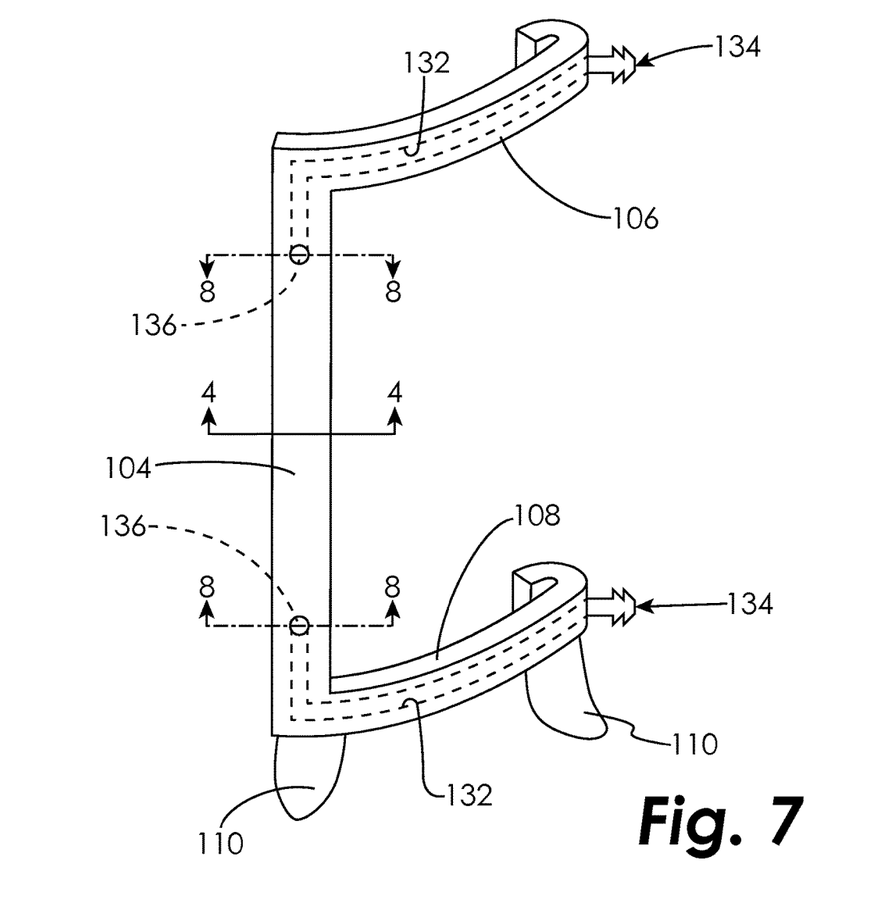
FIG. 7 is a schematic perspective view of a transducer position guide in an embodiment.
Figure 8:
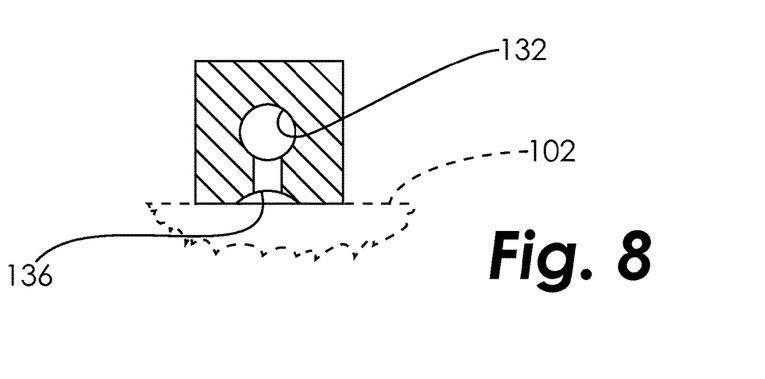
FIG. 8 is a schematic cross-sectional view of a transducer position guide in an embodiment.

In an embodiment illustrated in FIGS. 7-8, a vacuum attachment system may be provided in at least one of the transducer head guide rail 104, first arm 106 and/or second arm 108. The vacuum attachment system may include an internal passageway 132 extending from a first opening 134 to at least one second opening 136. The at least one second opening 136 is disposed adjacent a surface of the airfoil 102. A source of vacuum may be applied to the first opening 134, such that a suction is produced at the at least one second opening 136, which will cause the transducer position guide 100 to be held against the airfoil 102. In an embodiment, a coupler 138 may be provided at the first opening 134 to facilitate connection to a source of vacuum. The transducer head guide rail 104, first arm 106 and/or second arm 108 may be made by a rapid prototyping process to provide the passageway 132 and openings 134 and 136 in an embodiment.

Figure 9:
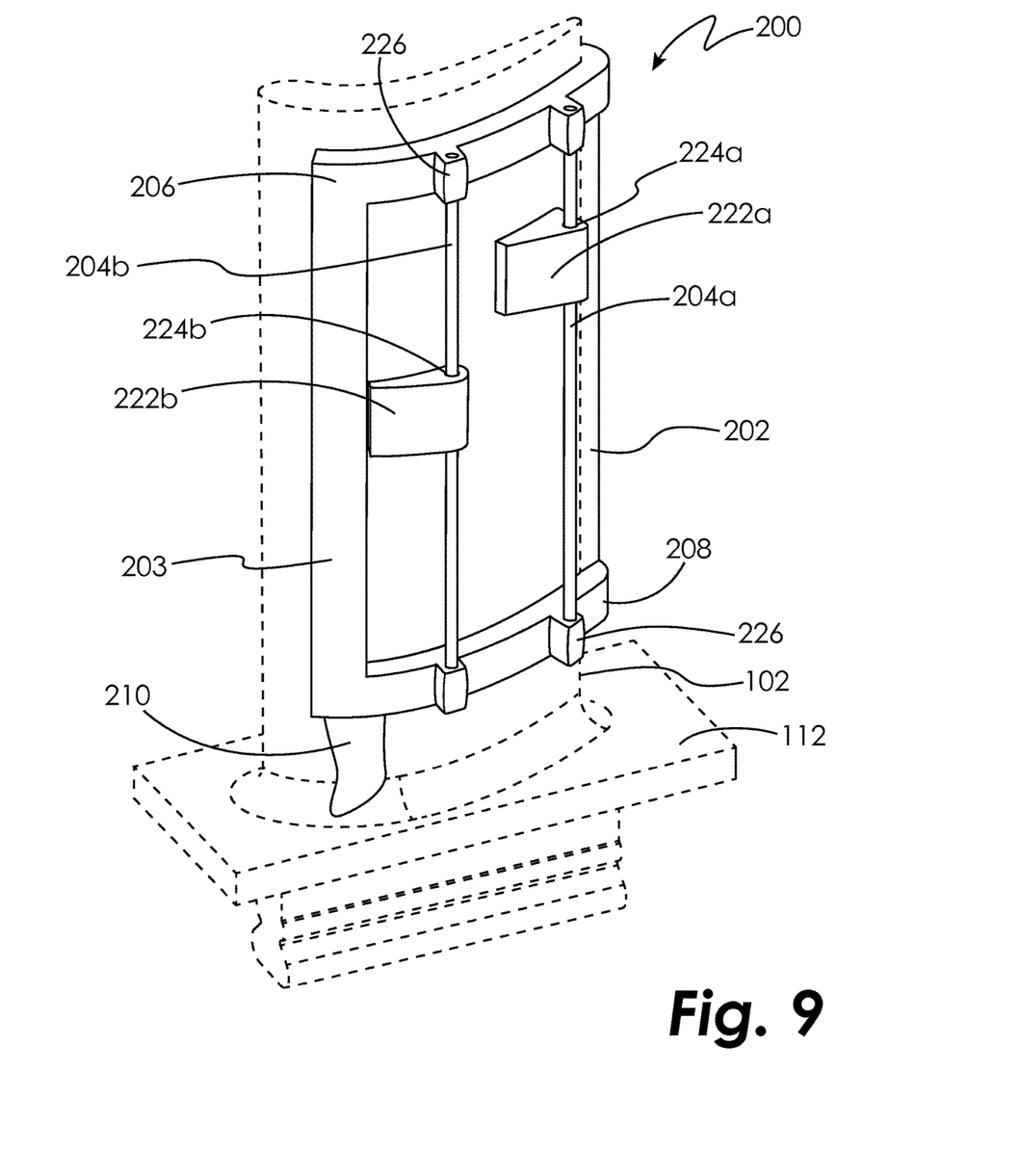
FIG. 9 is a schematic perspective view of a transducer position guide in an embodiment.

FIG. 9 illustrates a transducer position guide in another embodiment, indicated generally at 200. The transducer position guide 200 may be positioned adjacent the surface of an airfoil 102. The transducer position guide 200 includes a transducer head guide rail 204, a first support 202, a second support 203, a first arm 206 and a second arm 208. First arm 206 and second arm 208 extend between the first support 202 and the second support 203 in an embodiment. The first arm 206 and the second arm 208 may be curved such that they substantially match the contour of the airfoil 102 in an embodiment. The first arm 206 and the second arm 208 may wrap around the trailing edge and/or leading edge of the airfoil 102 to maintain the axial position of the transducer position guide 200 with respect to the airfoil 102 in an embodiment. The transducer position guide 200 may include at least one standoff 210 disposed on second arm 208, wherein the at least one standoff 210 rests upon a root 112 of the airfoil 102 in an embodiment. The standoff 210 maintains a desired radial location of the transducer position guide 200. In one embodiment, only a single standoff 210 is provided. In other embodiments, multiple standoffs 210 are provided.

The transducer position guide 200 includes at least one transducer head guide rail 204. The embodiment illustrated in FIG. 9 includes two transducer head guide rails 204a and 204b. Each transducer head guide rail 204 has a transducer head adaptor 222 disposed in sliding contact with the respective transducer head guide rail 204. The embodiment illustrated in FIG. 9 includes two transducer head adaptors 222a and 222b. Each transducer head adaptor 222a/222b may include a respective opening 224a/224b formed therein through which a respective transducer head guide rail 204a/204b passes in an embodiment. First arm 206 and second arm 208 may include transducer head guide rail mounts 226 extending therefrom. The transducer head guide rails 204 may be affixed to the transducer head guide rail mounts 226 in order to position each transducer head guide rail 204 at a desired location with respect to the airfoil 102 surface. In other embodiments, the transducer head guide rail 204 may be affixed to the first arm 206 and/or second arm 208 in other ways, the means of attachment not being critical. As with the transducer head adaptor 122, the transducer head adaptor 222 may include a transducer receiving cavity (not shown) to maintain a desired orientation between the transducer (not shown) and the surface of the airfoil 102. The transducer may be coupled to any desired test equipment by, for example, a wired or wireless connection. The transducer head adaptor 222 may then be translated along the transducer head guide rail 204 between the first arm 206 and the second arm 208 in order to produce a series of measurements.

While the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed:

1. A transducer position guide configured for application to an airfoil including an airfoil root, an airfoil body, an airfoil leading edge and an airfoil trailing edge, the transducer position guide comprising:
   a transducer head guide rail;
   at least one arm extending from the transducer head guide rail, the at least one arm matching the contour of the airfoil; and
   a transducer head adaptor configured to receive a transducer head, the transducer head adaptor disposed in sliding contact with the transducer head guide rail.

2. The transducer position guide of claim 1, wherein each of said at least one arm is curved to substantially match a contour of the airfoil body.

3. The transducer position guide of claim 1, wherein the at least one arm comprises a first arm and a second arm.

4. The transducer position guide of claim 1, further comprising:
   at least one standoff coupled to at least one of the transducer head guide rail and the at least one arm, the at least one standoff configured to contact the airfoil root when the transducer position guide is applied to the airfoil body.

5. The transducer position guide of claim 1, wherein at least one of the at least one arm includes a hooked distal portion configured to extend around the airfoil trailing edge when the transducer position guide is applied to the airfoil body.

6. The transducer position guide of claim 1, wherein at least one of the at least one arm includes a hooked proximal portion configured to extend around the airfoil leading edge when the transducer position guide is applied to the airfoil body.

7. The transducer position guide of claim 1, wherein the transducer guide rail is positioned parallel to a stacking axis of the airfoil when the transducer position guide is applied to the airfoil body.

8. The transducer position guide of claim 1, wherein the transducer guide rail includes an aft surface that forms an acute angle with the airfoil body when the transducer position guide is applied to the airfoil body.

9. The transducer position guide of claim 8, wherein the transducer head adaptor includes a forward surface that contacts the aft surface of the transducer guide rail, the forward surface of the transducer head adaptor forming an obtuse angle with the airfoil body when the transducer position guide is applied to the airfoil body.

10. The transducer position guide of claim 9, wherein the acute angle added to the obtuse angle equals substantially 180 degrees.

11. The transducer position guide of claim 1, wherein the transducer head adaptor includes a cavity formed therein to receive the transducer head.

12. The transducer position guide of claim 1, further comprising a vacuum attachment system disposed in at least one of the transducer head guide rail and the at least one arm.

13. The transducer position guide of claim 12, wherein the vacuum attachment system comprises an internal passageway extending from a first opening to at least one second opening, the at least one second opening being disposed adjacent a surface of the airfoil when the transducer position guide is applied to the airfoil body.

14. A transducer position guide configured for application to an airfoil including an airfoil root, an airfoil body, an airfoil leading edge and an airfoil trailing edge, the transducer position guide comprising:
   a first support;
   at least one arm extending from the first support, the at least one arm matching the contour of the airfoil;
   a transducer head guide rail coupled to the at least one arm; and
   a transducer head adaptor configured to receive a transducer head, the transducer head adaptor disposed in sliding contact with the transducer head guide rail.

15. The transducer position guide of claim 14, wherein said at least one arm comprises a first arm and a second arm.

16. The transducer position guide of claim 15, further comprising a second support, wherein the first arm and the second arm extend between the first and second supports.

17. The transducer position guide of claim 14, further comprising:
   at least one standoff coupled to the at least one arm, the at least one standoff configured to contact the airfoil root when the transducer position guide is applied to the airfoil body.

18. The transducer position guide of claim 14, wherein the transducer head adaptor includes an opening formed therethrough and the transducer head guide rail passes through the opening.

19. The transducer position guide of claim 14, wherein:
   the transducer head guide rail comprises a first transducer head guide rail and a second transducer head guide rail;
   the transducer head adaptor comprises a first transducer head adaptor and a second transducer head adaptor;
   the first transducer head adaptor is disposed in sliding contact with the first transducer head guide rail; and
   the second transducer head adaptor is disposed in sliding contact with the second transducer head guide rail.

20. The transducer position guide of claim 14, further comprising at least one transducer head guide rail mount coupling the transducer head guide rail to the at least one arm.

* * * * *